US009683988B2

(12) United States Patent
Wang et al.

(10) Patent No.: US 9,683,988 B2
(45) Date of Patent: Jun. 20, 2017

(54) CELL MODEL AND METHOD FOR SCREENING C-FMS KINASE INHIBITORS

(75) Inventors: Lili Wang, Beijing (CN); Shengqian Yang, Beijing (CN); Long Long, Beijing (CN); Junhai Xiao, Beijing (CN); Song Li, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 499 days.

(21) Appl. No.: 14/008,093

(22) PCT Filed: Mar. 14, 2012

(86) PCT No.: PCT/CN2012/072326
§ 371 (c)(1),
(2), (4) Date: Nov. 13, 2013

(87) PCT Pub. No.: WO2012/130042
PCT Pub. Date: Oct. 4, 2012

(65) Prior Publication Data
US 2014/0057804 A1 Feb. 27, 2014

(30) Foreign Application Priority Data

Mar. 30, 2011 (CN) .......................... 2011 1 0077710

(51) Int. Cl.
| | |
|---|---|
| C12N 5/02 | (2006.01) |
| G01N 33/50 | (2006.01) |
| C12Q 1/48 | (2006.01) |
| C07K 14/715 | (2006.01) |
| C07K 14/47 | (2006.01) |

(52) U.S. Cl.
CPC ..... *G01N 33/5035* (2013.01); *C07K 14/4705* (2013.01); *C07K 14/7153* (2013.01); *C12Q 1/485* (2013.01); *C12Y 207/01112* (2013.01); *G01N 2500/10* (2013.01)

(58) Field of Classification Search
None
See application file for complete search history.

(56) References Cited

PUBLICATIONS

English translation of the IPRP for PCT/CN2012/072326 mailed Oct. 2, 2013, pp. 1-11.
English translation of the International Search Report for PCT/CN2012/072326 mailed Jul. 5, 2012, pp. 1-4.
Yang, et al., "Establishment of mTEL-cFmskd eukaryotic expression vector and its effect on STAT1/3 nuclear translocation," Chin. J. Pharmacol. Toxicol., Oct. 31, 2011, vol. 25, No. 5, pp. 456-462, ISSN: 1000-3002.
Novak, et al., "Colony-stimulating factor 1-induced STAT1 and STAT3 activation is accompanied by phosphorylation of Tyk2 in macrophages and Tyk2 and JAK1 in fibroblasts," Blood, Oct. 15, 1995, vol. 86, No. 8, pp. 2948-2956, ISSN: 0006-4971.
Huang, et al., "Establishment of high-throughput drug screening cell models based on JAK-STAT signal pathway," Acta. Pharmaceutica. Sinica., Mar. 31, 2004, vol. 39, No. 3, pp. 164-167, ISSN: 0513-4870.
Yang, et al., "Macrophage colony-stimulating factor receptor and its inhibitors: research advances," J. Int. Pharm. Res., Oct. 31, 2010, vol. 37, No. 5, pp. 340-345, ISSN: 1674-0440.
Sherr, et al., "Colony-stimulating factor-1 receptor (c-fms)," [J] J. Cell Biochem., 1988, vol. 38, No. 3, pp. 179-187.
Douglass, et al., "Macrophage colony-stimulating factor" not just for macrophages anymore! A gateway into complex biologies, [J] Int. Immunopharmacol, 2008, vol. 8, No. 10, pp. 1354-1376.
Hamilton, J. A., "CSF-1 and cell cycle control in macrophages," [J]. Mol. Reprod. Dev., 1997, vol. 46, pp. 19-23.
Guo, et al., "Inhibition of phyosphorylation of the colony-stimulating factor-1 receptor (c-Fms) tyrosine kinase in transfected cells by ABT-869 and other tyrosine kinase inhibitors," Molecular Cancer Therapeutics, 2006, vol. 5, pp. 1007-1013.
Zhang, et al., "A Simple Statistical Parameter for Use in Evaluation and Validation of High Throughput Screening Assays," [J]. J. Biomol. Screen, 1999, vol. 4, No. 2, p. 67-73.
English summary of first Office Action from SIPO for CN Application No. 102719404 A, 1 page.
Supplemental Search Report for European Appl. No. 12762924.4 dated Nov. 25, 2014.
Koester, et al., "Dynamic redistribution of STAT1 protein in IFN signaling visualized by GFP fusion proteins", European Journal of Biochemistry, vol. 260, No. 1, Feb. 1999, pp. 137-144.
Mashkani, et al., "Colony stimulating factor-1 receptor as a target for small molecule inhibitors", Bioorganic & Medicinal Chemistry, vol. 18, No. 5, Mar. 1, 2010, pp. 1789-1797.
Osmond, et al., "Development of cell-based assays for cytokine receptor signaling, using AlphaScreen SureFire assay format", Analytical Biochemistry, vol. 403, No. 1-2, Aug. 1, 2010, pp. 94-101.
Patel, et al., "Colony-stimulating factor-1 receptor inhibitors for the treatment of cancer and inflammatory disease", Current Topics in Medicinal Chemistry, vol. 9, No. 7, Jan. 1, 2009, pp. 599-610.
Japanese Office Action mailed on Apr. 28, 2015 for JP Patent Application No. 2014-501412, with English translation, 8 pages.
Japanese Office Action mailed on Dec. 8, 2015 for JP Patent Application No. 2014-501412, with English translation, 4 pages.

(Continued)

*Primary Examiner* — Michael Pak
(74) *Attorney, Agent, or Firm* — Kilpatrick Townsend and Stockton LLP

(57) ABSTRACT

The present invention provides a cell model and a method for screening c-Fms tyrosine kinase inhibitors. Specifically, the present invention provides a cell that expresses macrophage colony stimulating factor receptor and STAT1 protein simultaneously. The present invention further provides a method for screening c-Fms tyrosine kinase inhibitors, a method for evaluating the inhibiting activity of a compound or a composition against c-Fms tyrosine kinase, and use of the cell in screening c-Fms tyrosine kinase inhibitors. The cell model established in the present invention is sensitive, highly effective and reliable, and can be used in high-throughput screening and/or high-content screening of c-Fms tyrosine kinase inhibitors.

1 Claim, 5 Drawing Sheets

(56) References Cited

PUBLICATIONS

Campagne, et al., "Nuclear magnetic resonance analysis of protein-DNA interactions", J. R. Soc. Interface, 8, 2011, 1065-1078.
Chalfie, "Green fluorescent protein", Photochemistry and Photobiology, 62(4), 1995, 651-656.
Dey, et al., "DNA-protein interactions: methods for detection and analysis", Mol. Cell. Biochem, 365, 2012, 279-299.
Fabian, et al., "A small molecule-kinase interaction map for clinical kinase inhibitors", Nature Biotechnology, 23(3), Mar. 2005, 329-336.
Guo, et al., "Inhibition of phosphorylation of the colony-stimulating factor-1 receptor (c-Fms) tyrosine kinase in transfected cells by ABT-869 and other tyrosine kinase inhibitors", Mol. Cancer Ther., 5(4), Apr. 2006, 1007-1013.
Roessel, et al., "Imagining into the future: visualizing gene expression and protein interactions with fluorescent proteins", Nature Cell Biology, 4, Jan. 2002, E15-E20.
Tsien, "The green fluorescent protein", Annu. Rev. Biochem., 67, 1998, 509-544.
Xie, et al., "Systematic characterization of protein-DNA interactions", Cell. Mol. Life Sci., 68, 2011, 1657-1668.

SEQUENCE LISTING

<160> NUMBER OF SEQ ID NOS: 2

<210> SEQ ID NO 1
<211> LENGTH: 2139
<212> TYPE: DNA
<213> ORGANISM: Homo sapiens

<400> SEQUENCE: 1

| | | | | | |
|---|---|---|---|---|---|
| atgtctcagt | ggtacgaact | tcagcagctt | gactcaaaat | tcctggagca | ggttcaccag | 60 |
| ctttatgatg | acagttttcc | catggaaatc | agacagtacc | tggcacagtg | gttagaaaag | 120 |
| caagactggg | agcacgctgc | caatgatgtt | tcatttgcca | ccatccgttt | tcatgacctc | 180 |
| ctgtcacagc | tggatgatca | atatagtcgc | ttttctttgg | agaataactt | cttgctacag | 240 |
| cataacataa | ggaaaagcaa | gcgtaatctt | caggataatt | ttcaggaaga | cccaatccag | 300 |
| atgtctatga | tcatttacag | ctgtctgaag | gaagaaagga | aaattctgga | aaacgcccag | 360 |
| agatttaatc | aggctcagtc | ggggaatatt | cagagcacag | tgatgttaga | caaacagaaa | 420 |
| gagcttgaca | gtaaagtcag | aaatgtgaag | gacaaggtta | tgtgtataga | gcatgaaatc | 480 |
| aagagcctgg | aagatttaca | agatgaatat | gacttcaaat | gcaaaacctt | gcagaacaga | 540 |
| gaacacgaga | ccaatggtgt | ggcaaagagt | gatcagaaac | aagaacagct | gttactcaag | 600 |
| aagatgtatt | taatgcttga | caataagaga | aggaagtag | ttcacaaaat | aatagagttg | 660 |
| ctgaatgtca | ctgaacttac | ccagaatgcc | ctgattaatg | atgaactagt | ggagtggaag | 720 |
| cggagacagc | agagcgcctg | tattgggggg | ccgcccaatg | cttgcttgga | tcagctgcag | 780 |
| aactggttca | ctatagttgc | ggagagtctg | cagcaagttc | ggcagcagct | taaaaagttg | 840 |
| gaggaattgg | aacagaaata | cacctacgaa | catgaccta | tcacaaaaaa | caaacaagtg | 900 |
| ttatgggacc | gcaccttcag | tcttttccag | cagctcattc | agagctcgtt | tgtggtggaa | 960 |
| agacagccct | gcatgccaac | gcaccctcag | aggccgctgg | tcttgaagac | aggggtccag | 1020 |
| ttcactgtga | agttgagact | gttggtgaaa | ttgcaagagc | tgaattataa | tttgaaagtc | 1080 |
| aaagtcttat | ttgataaaga | tgtgaatgag | agaaatacag | taaaaggatt | taggaagttc | 1140 |
| aacattttgg | gcacgcacac | aaaagtgatg | aacatggagg | agtccaccaa | tggcagtctg | 1200 |
| gcggctgaat | ttcggcacct | gcaattgaaa | gaacagaaaa | atgctggcac | agaacgaat | 1260 |
| gagggtcctc | tcatcgttac | tgaagagctt | cactcccta | gttttgaaac | ccaattgtgc | 1320 |
| cagcctggtt | tggtaattga | cctcgagacg | acctctctgc | ccgttgtggt | gatctccaac | 1380 |
| gtcagccagc | tcccgagcgg | ttgggcctcc | atcctttggt | acaacatgct | ggtggcggaa | 1440 |
| cccaggaatc | tgtccttctt | cctgactcca | ccatgtgcac | gatgggctca | gctttcagaa | 1500 |
| gtgctgagtt | ggcagttttc | ttctgtcacc | aaaagaggtc | tcaatgtgga | ccagctgaac | 1560 |
| atgttgggag | agaagcttct | tggtcctaac | gccagcccg | atggtctcat | tccgtggacg | 1620 |
| aggttttgta | aggaaaatat | aaatgataaa | aattttccct | tctggctttg | gattgaaagc | 1680 |
| atcctagaac | tcattaaaaa | acacctgctc | cctctctgga | atgatgggtg | catcatgggc | 1740 |
| ttcatcagca | aggagcgaga | gcgtgccctg | ttgaaggacc | agcagccggg | gaccttcctg | 1800 |
| ctgcggttca | gtgagagctc | ccgggaaggg | gccatcacat | tcacatgggt | ggagcggtcc | 1860 |
| cagaacggag | gcgaacctga | cttccatgcg | gttgaaccct | acgaagaa | agaactttct | 1920 |
| gctgttactt | tccctgacat | cattcgcaat | tacaaagtca | tggctgctga | gaatattcct | 1980 |
| gagaatcccc | tgaagtatct | gtatccaaat | attgacaaag | accatgcctt | tggaaagtat | 2040 |
| tactccaggc | caaaggaagc | accagagcca | atggaacttg | atggccctaa | aggaactgga | 2100 | tatatcaaga ctgagttgat ttctgtgtct gaagtgtaa                           2139

<210> SEQ ID NO 2
<211> LENGTH: 2919
<212> TYPE: DNA
<213> ORGANISM: Homo sapiens

<400> SEQUENCE: 2
atgggcccag gagttctgct gctcctgctg gtggccacag cttggcatgg tcagggaatc     60
ccagtgatag agcccagtgt ccctgagctg gtcgtgaagc aggagcaac ggtgaccttg     120 cgatgtgtgg gcaatggcag cgtggaatgg gatggccccc catcacctca ctggaccctg    180
tactctgatg gctccagcag catcctcagc accaacaacg ctaccttcca aaacacgggg    240
acctatcgct gcactgagcc tgagacccc ctgggaggca gcgccgccat ccacctctat    300
gtcaaagacc ctgcccggcc ctggaacgtg ctagcacagg aggtggtcgt gttcgaggac    360
caggacgcac tactgccctg tctgctcaca gacccggtgc tggaagcagg cgtctcgctg    420
gtgcgtgtgc gtggccggcc cctcatgcgc acaccaact actccttctc gccctggcat    480
ggcttcacca tccacagggc caagttcatt cagagccagg actatcaatg cagtgccctg    540
atgggtggca ggaaggtgat gtccatcagc atccggctga agtgcagaa agtcatccca    600 gggcccccag ccttgacact ggtgcctgca gagctggtgc ggattcgagg ggaggctgcc    660
cagatcgtgt gctcagccag cagcgttgat gttaactttg atgtcttcct ccaacacaac    720
aacaccaagc tcgcaatccc tcaacaatct gactttcata ataaccgtta ccaaaaagtc    780
ctgaccctca acctcgatca agtagatttc caacatgccg gcaactactc ctgcgtggcc    840
agcaacgtgc agggcaagca ctccaccctc atgttcttcc gggtggtaga gagtgcctac    900
ttgaacttga gctctgagca gaacctcatc caggaggtga ccgtggggga ggggctcaac    960
ctcaaagtca tggtggaggc ctacccaggc ctgcaaggtt taactggac ctacctggga    1020 cccttttctg accaccagcc tgagcccaag cttgctaatg ctaccaccaa ggacacatac    1080
aggcacacct tcaccctctc tctgccccgc ctgaagccct ctgaggctgg ccgctactcc    1140
ttcctggcca aaacccagg aggctggaga gctctgacgt ttgagctcac ccttcgatac    1200
cccccagagg taagcgtcat atggacattc atcaacggct ctggcacccct tttgtgtgct    1260 gcctctgggt accccccagcc caacgtgaca tggctgcagt gcagtggcca cactgatagg    1320
tgtgatgagg cccaagtgct gcaggtctgg gatgacccat accctgaggt cctgagccag    1380
gagcccttcc acaaggtgac ggtgcagagc ctgctgactg ttgagacctt agagcacaac    1440
caaacctacg agtgcagggc ccacaacagc gtggggagtg gctcctgggc cttcataccc    1500
atctctgcag gagcccacac gcatccccg gatgagttcc tcttcacacc agtggtggtc    1560
gcctgcatgt ccatcatggc cttgctgctg ctgctgctcc tgctgctatt gtacaagtat    1620
aagcagaagc ccaagtacca ggtccgctgg aagatcatcg agagctatga gggcaacagt    1680
tatacttcca tcgaccccac gcagctgcct tacaacgaga gtgggagtt ccccggaac    1740 aacctgcagt ttggtaagac cctcggagct ggagcctttg gaaggtggt ggaggccacg    1800 gcctttggtc tgggcaagga ggatgctgtc ctgaaggtgg ctgtgaagat gctgaagtcc    1860
acggcccatg ctgatgagaa ggaggccctc atgtccgagc tgaagatcat gagccacctg    1920
ggccagcacg agaacatcgt caaccttctg gagcctgta cccatggagg ccctgtactg    1980
gtcatcacgg agtactgttg ctatggcgac ctgctcaact ttctgcgaag gaaggctgag    2040
gccatgctgg gacccagcct gagccccggc caggaccccg agggaggcgt cgactataag    2100

-continued

```
aacatccacc tcgagaagaa atatgtccgc agggacagtg gcttctccag ccagggtgtg    2160
gacacctatg tggagatgag gcctgtctcc acttcttcaa atgactcctt ctctgagcaa    2220
gacctggaca aggaggatgg acggccctg gagctccggg acctgcttca cttctccagc    2280
caagtagccc agggcatggc cttcctcgct tccaagaatt gcatccaccg ggacgtggca    2340
gcgcgtaacg tgctgttgac caatggtcat gtggccaaga ttggggactt cgggctggct    2400
agggacatca tgaatgactc caactacatt gtcaagggca atgcccgcct gcctgtgaag    2460
tggatggccc cagagagcat ctttgactgt gtctacacgg ttcagagcga cgtctggtcc    2520
tatggcatcc tcctctggga gatcttctca cttgggctga atccctaccc tggcatcctg    2580
gtgaacagca agttctataa actggtgaag gatggatacc aaatggccca gcctgcattt    2640
gccccaaaga atatatacag catcatgcag gcctgctggg ccttggagcc cacccacaga    2700
cccaccttcc agcagatctg ctccttcctt caggagcagg cccaagagga caggagagag    2760
cgggactata ccaatctgcc gagcagcagc agaagcggtg gcagcggcag cagcagcagt    2820
gagctggagg aggagagctc tagtgagcac ctgacctgct gcgagcaagg ggatatcgcc    2880
cagcccttgc tgcagcccaa caactatcag ttctgctga                          2919
```

CELL MODEL AND METHOD FOR SCREENING C-FMS KINASE INHIBITORS

PRIORITY CLAIM

This is a national stage application of PCT/CN2012/072326 filed Mar. 14, 2012, which claims priority to CN Application No. 201110077710.0, filed Mar. 30, 2011, the entire contents and disclosures of which are incorporated herein by reference.

TECHNICAL FIELD

The invention belongs to the field of cytobiology and pharmacy, and relates to a cell model and a method for screening c-Fms kinase inhibitors.

BACKGROUND ART

Drug screening model is an indispensible platform for drug activity research in the drug research and development. High Content Analysis or High Content Screening (HCS) is an automatic platform utilizing high-throughput fluorescence/bright field microscopic imaging and quantitative image analysis integrated with open reagents and fluorescence labeling technique, which can detect impact to cells by samples to be screened in various aspects, such as cellular morphology, growth, differentiation, migration, apoptosis, metabolic pathway and signal transduction simultaneously, obtain a lot of relevant information in a single experiment so as to determine the biological activity and potential toxicity while keeping the cell structure and function integral. It is an inevitable tendency for creative drug screening research to establish a cell model for screening kinase inhibitors and to combine it with high-throughput screening technique on the basis of High Content technique.

Kinase as target for drugs (such as anti-tumor drugs) has become a hotspot for the new drug development internationally. Macrophage colony stimulating factor receptor kinase (c-Fms, CSF-1R) is a product encoded by protooncogene c-fms, and belongs to the type ° C. tyrosine kinase family, as stem cell growth factor receptor(c-Kit), platelet-derived growth factor receptor (PDGFR), Fms-like tyrosine kinase 3 (Flt-3) and so on. After binding to macrophage colony stimulating factor (M-CSF, CSF-1), the tyrosine kinase activity of c-Fms is activated, promotes the survival, proliferation and proliferation of mononuclear macrophage cell line (Sherr C. J., Roussel M. F., Rettenmier C. W., Colony-stimulating factor-1 receptor (c-fms)[J]. J. Cell Biochem., 1988, 38(3):179-187). Factors such as repeated replication, mutation, chromosome translocation of C-fms gene and over-expression of M-CSF can abnormally enhance c-Fms kinase activity, result in abnormal proliferation of mononuclear macrophage or high expression of relevant inflammatory factors, and finally lead to the development of diseases such as hematopoietic system disorder, malignant tumors, inflammation and atherosclerosis.

C-Fms inhibitors, which can inhibit the phosphorylation of receptor kinases and block cell signal pathway mediated by receptor kinases, are candidate drugs for treating c-Fms-related diseases (Douglass T. G., Driggers L., Zhang J. G., et al., Macrophage colony-stimulating factor: not just for macrophages anymore! A gateway into complex biologies [J]. Int. Immunopharmacol, 2008, 8(10): 1354-1376). Signal transducer and transcription activator (STAT1) which are important molecules of cell signal downstream of c-Fms kinases, enter nucleus upon activation by c-Fms, and activate the transcription of relevant genes (Hamilton J. A., CSF-1 and cell cycle control in macrophages [J]. Mol. Reprod. Dev., 1997, 46(1): 19-23). The extent of STAT1 nuclear translocation directly reflects the kinase activity of c-Fms.

As reported in current documents, methods for screening c-Fms inhibitors mainly includes methods for determining kinase activity at the molecular level and methods of western blot for detecting kinase phosphorylation at cellular level, however, they have shortcomings such as complex and tedious operations and low quantification extent. In addition, since the phosphorylation of receptor kinases such as c-Fms occurs in a short time, it is difficult to detect it accurately. Furthermore, due to easy dimerization in vitro and the like, there is no report on cell models of high-throughput screening of c-Fms inhibitors based on High Content Analysis.

CONTENTS OF INVENTION

With creative work and large quantity of experiments, the inventors established a cell model, and found that the screening of c-Fms kinase inhibitors could be accomplished by analysis of STAT1 nuclear translocation in the cells. Therefore, the invention is provided as follows:

In one aspect, the present invention relates to a cell that expresses macrophage colony stimulating factor receptor and STAT1 protein simultaneously.

The cell according to any item of the present invention meets one or more of the following items (1)-(3):
(1) said macrophage colony stimulating factor receptor originates from human, sepcifically, is c-Fms;
(2) said STAT1 protein is linked with a detectable label; specifically, said detectable label is a reporter gene; more specifically, said reporter gene is green fluorescence protein (GFP); and
(3) said cell is a mammalian cell that is cultured in vitro, preferably a human osteosarcoma cell (such as human osteosarcoma cell U2OS).

The cell of the present invention can be used for screening tyrosine kinase inhibitors or evaluating the inhibiting activity to tyrosine kinase of a compound or a composition, namely, it can be used as a cell model for screening tyrosine kinase inhibitors or evaluating the inhibiting activity to tyrosine kinase of a compound or a composition. Specifically, said tyrosine kinase is macrophage colony stimulating factor receptor kinase, more specifically, is c-Fms. The Example 4 of the present invention demonstrates the feasibility of the cell model.

In the cell model, the activity of c-Fms kinase may be reflected by the extent of nuclear translocation of the protein molecules of cell signal downstream mediated by receptor kinase. When the cell model is used to screen tyrosine kinase inhibitors, the extent of nuclear translocation of the protein molecules downstream is detected to evaluate the inhibiting activity of a compound against c-Fms kinase.

The cell can be prepared by the following steps:
1) constructing an eukaryotic expression vector comprising human macrophage colony stimulating factor receptor gene;
2) transfecting a human osteosarcoma cell stably expressing STAT1 protein (such as GFP-STAT1 fusion protein), with the above vector; and
3) screening the cell line that stably expresses human macrophage colony stimulating factor receptor and STAT1 protein (such as GFP-STAT1 fusion protein).

The cell of the present invention can also be produced by co-transfecting a human osteosarcoma cell with a vector comprising human macrophage colony stimulating factor receptor gene such as c-Fms, and a vector comprising STAT1 gene such as GFP-STAT1 gene.

In another aspect, the present invention relates to a cell strain (human osteosarcoma cell strain, U2OS-GFP-STAT1/CSF-1R), which was deposited in China General Microbiological Culture Collection Center, with an accession number of CGMCC No. 4688 and a deposit date of Mar. 22, 2011.

The cell strain is human osteosarcoma cell U2OS that can stably express c-Fms and GFP-STAT1 fusion protein.

In another aspect, the present invention relates to a method for screening c-Fms tyrosine kinase inhibitors or evaluating the inhibiting activity of a compound or a composition against tyrosine kinase, comprising the step of using the cell according to any item of the present invention, or the cell strain of the present invention.

A method for screening c-Fms tyrosine kinase inhibitors or evaluating the inhibiting activity of a compound or a composition against tyrosine kinase according to any item of the present invention, comprises the following steps:

after treating the cell with the compound or the composition for at least 1 hour, activating macrophage colony stimulating factor receptor kinase with macrophage colony stimulating factor, detecting and analyzing the extent of nuclear translocation of STAT1, and evaluating the inhibiting activity of the compound or the composition against tyrosine kinase.

The method for screening c-Fms tyrosine kinase inhibitors according to any item of the present invention, comprises the following steps:
1) seeding and culturing the cell according to any item of the present invention or the cell strain of the present invention;
2) discarding the medium, and washing the cell with serum-free medium at least once;
3) adding the compound or composition to be tested, and culturing the cell in serum-free medium;
4) adding macrophage colony stimulating factor and continuing the culturing in serum-free medium; and
5) analyzing the extent of nuclear translocation of STAT1 protein, and evaluating the activity of the compound or the composition.

The method for screening c-Fms tyrosine kinase inhibitors according to any item of the present invention, wherein the culturing time after adding macrophage colony stimulating factor is from 5 to 35 minutes, preferably from 20 to 35 minutes, such as 20, 21, 22, 23, 24, 25, 26, 27, 28, 29, 30, 31, 32, 33, 34, or 35 minutes, and more preferably 30 minutes.

The method for screening c-Fms tyrosine kinase inhibitors according to any item of the present invention, wherein when macrophage colony stimulating factor is added, its final concentration ranges from 30 ng/ml to 1000 ng/ml, preferably from 100 to 600 ng/ml, more preferably from 150 to 250 ng/ml, and particularly preferably 200 ng/ml.

The method for screening c-Fms tyrosine kinase inhibitors according to any item of the present invention, meets one or more of the following items (1)-(5):
(1) said cell in step 1) was seeded with a density of $6 \times 10^4$-$12 \times 10^4$ cells/ml based on a 96-well plate, and the culturing time is from 12 to 48 hours, preferably 24 hours;
(2) the conditions of culturing in step 1), 3) or 4) are 37° C., 5% $CO_2$, 80% humidity;
(3) the serum-free medium in step 2), 3) or 4) contains 0.2% BSA and 10 mM HEPES;
(4) in step 3), after the adding of the compound or the composition to be tested, the culturing time is from 0.5 to 1.5 hours, preferably 1 hour;
(5) before analyzing the extent of nuclear translocation of STAT1 protein in step 5), the following pretreatment steps are comprised: fixing the cells with a PBS-diluted formaldehyde solution; placing the cells in dark at room temperature for 20 minutes; discarding the solution; adding PBS that contains nuclear dye hoechst33342; and placing the cells in dark at room temperature for 30 minutes.

The above mentioned method for screening c-Fms tyrosine kinase inhibitors can also be used as the method for evaluating the inhibiting activity of a compound or a composition against tyrosine kinase.

In a further aspect, the present invention relates to the use of the cell according to any item of the present invention or the cell strain of the present invention for screening c-Fms tyrosine kinase inhibitors or evaluating the inhibiting activity of a compound or a composition against c-Fms tyrosine kinase.

In the present invention, STAT1 and c-Fms may refer to the sequences with GenBank accession number of BC002704 and NM005211, and their nucleotide sequences are set forth in SEQ ID NO: 1 and SEQ ID NO: 2, respectively. However, in the present invention, the sequences of STAT1 and c-Fms are not limited to the sequences set forth in SEQ ID NO: 1 and SEQ ID NO: 2, the sequences, which are resulted from one or more substitutions, replacements, deletions of the sequences set forth in SEQ ID NO: 1 and SEQ ID NO: 2 and have the function of STAT1 or c-Fms, are also within the scope of the present invention. The present invention also comprises the sequences which have an homology of more than 70%, more than 80%, more than 90%, more than 95%, more than 96%, more than %, more than 98%, or more than 99% to SEQ ID NO: 1 or SEQ ID NO: 2 and have the function of STAT1 or c-Fms.

In the present invention, specifically, said tyrosine kinase can be c-Fms tyrosine kinase.

Advantageous Effects of the Invention

The cell model established in the present invention is sensitive, highly effective, reliable, and can be used in the high-throughput screening and/or high content screening of c-Fms tyrosine kinase inhibitors. The screening method established in the present invention has a higher sensitivity than western blot method and its operation is simple and fast.

ABOUT THE REFERENCE OF DEPOSIT OF THE BIOLOGICAL MATERIAL

Figure 1A:
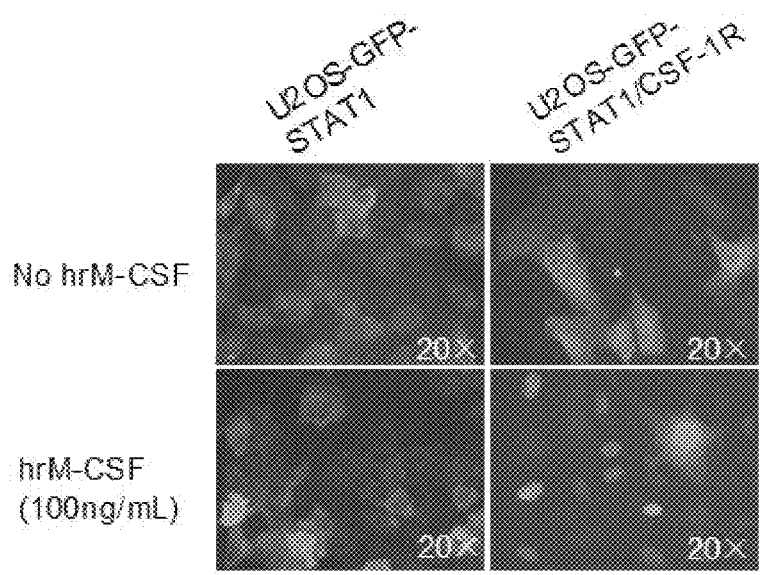
FIG. 1: GFP-STAT1 nuclear translocation induced by hrM-CSF in cells expressing human c-Fms (FIG. 1A-B).

The invention relates to the following biological material:

Human osteosarcoma cell strain (U20S-GFP-STAT1/CSF-1R), which was deposited in China General Microbiological Culture Collection Center (CGMCC) on Mar. 22, 2011, with an accession number of CGMCC No. 4688. The deposit address is NO. 3 of yihaoyuan, Beichen West Road, Chaoyang District, Beijing 100101, China.

SPECIFIC MODE FOR CARRYING OUT THE INVENTION (1) The embodiments of the invention are illustrated in detail via the following examples. However, a person skilled in the art would understand that the following examples are only intended to illustrate the invention, rather than being considered to limit the scope of the invention. Under the circumstance wherein the specific techniques or conditions are not indicated in the Examples, the inventions are carried out according to the techniques or conditions described in the literature of the art (for example, Sambrook. J. et al., Molecular Cloning: A laboratory Manual, translated by Huang Peitang et al., 3rd edition, Science Press) or according to the specifications of the products. The reagents or apparatuses, of which the manufacturers are not indicated, are conventional products that are commercially available.

Main drugs and reagents: Plasmid MiniPrep Kit, purchased from Omega Bio-tek Co.; restriction endonucleases, T4 ligase, purchased from TaKaRa Co.; liposome 2000, hoechst33342 dye, purchased from Invitrogen Co.; DMEM (High glucose), purchased from Gibco Co.; fetal bovine serum purchased from Tianjin Chuanye Biochemicals Co., Ltd.; neomycin (G418), puromycin, purchased from Merck Co.; hrM-CSF factor, purchased from Peprotech Co.; BSA, HEPES, purchased from Amresco Co.; all the kinase inhibitors used in the invention were synthesized by the inventors; the rest agents are analytical reagents produced in China.

Main apparatus: In Cell Analyzer 1000 or In Cell Analyzer 2000 GE healthcare life science.

Cell line: U2OS-GFP-STAT1 human osteosarcoma cell Thermo (Bio Image).

Example 1: Establishment of a Cell Line Stably Expressing Human c-Fms and STAT1

(1) A eukaryotic expression vector pCORON/puro-cfms comprising full-length cDNA of human c-Fms (donated by Dr. Charles Sherr and Dr. Martine Roussel from St. Jude Children's Research Hospital, USA) was constructed, and a human osteosarcoma cell line wherein GFP and STAT1 were fused and expressed, was transfected with the vector by lipofectin.

A new cell line stably expressing human c-Fms was obtained by means of resistance screening and limiting dilution. DMEM medium that contains 4500 mg/L glucose, 10% fetal bovine serum, 4 mM L-glutamine, 500 m/mL G418 and 2 μg/mL puromycin was used, and the cell line was cultured in an incubator at 37° C., 5% $CO_2$, 80% humidity.

Compared with the cells prior to transfection, the established cell had no significant change in cellular morphology, and had a stable growth state.

The cell line prepared in this example (i.e. the human osteosarcoma cell line of the present invention which was deposited with an accession number of CGMCC No. 4688) can be used as a cell model for screening tyrosine kinase inhibitors or evaluating the inhibiting activity of a compound against tyrosine kinase.

Example 2: Characterization of the Newly Established Cell Line

The cell line prepared in the Example 1 was treated with recombinantly expressed human M-CSF(hrM-CSF), so as to activate c-Fms and induce GFP-STAT1 nuclear translocation. In the established cell line, human macrophage colony stimulating factor receptors were dimerized upon binding to the specific ligand M-CSF, and meanwhile the steric conformation was changed and the kinase domain was activated. The downstream signal pathway of c-Fms was activated by transphosphorylation. The phosphorylated GFP-STAT1 were also dimerized and entered nucleus, namely, nuclear translocation occurred.

In order to quantitatively detect the extent of nuclear translocation of GFP-STAT1 induced by hrM-CSF, in this Example, in Cell Analyzer 1000 or In Cell Analyzer 2000 was used to obtain the cell image of GFP-STAT1 nuclear translocation. The cell image obtained was analyzed by using Nuclear Trafficking Analysis Module, wherein the translocation index represents the extent of nuclear translocation of GFP-STAT1. Translocation index equals to the ratio of the mean fluorescence intensity of nucleus to the mean fluorescence intensity of cytoplasm of the cells obtained per well. The steps were as follows:

1) seeding the cells to a 96-well culture plate (which was black and transparent at the bottom), culturing in an incubator at 37° C., 5% $CO_2$, 80% humidity for 24 hours;
2) washing the cell twice with serum-free DMEM medium that contains 4500 mg/L glucose, 4 mM L-glutamine, 0.2% BSA and 10 mM HEPES (hereafter referred to as cell analytic liquid), wherein the cell analytic liquid was added at 100 μL/well for each time; after that, adding 50 μL cell analytic liquid to each well;
3) adding the cell analytic liquid that contains hrM-CSF at 50 μL/well, to obtain a final hrM-CSF concentration of 100 ng/mL, and incubating the cells in an incubator at 37° C. for 30 minutes;
4) fixing the cells with 8% formaldehyde diluted with 1×PBS solution and preheated at 37° C. at 100 μL/well, and placing the plate in dark at room temperature for 20 minutes;
5) discarding the cell fixation solution, adding 1×PBS solution that contains hoechst33342 at 200 μL/well, placing the plate in dark at room temperature for 30 minutes;
6) obtaining the cell image by using In Cell Analyzer 1000, analyzing the extent of nuclear translocation of GFP-STAT1 by using Nuclear Trafficking Analysis Module.

Figure 1B:
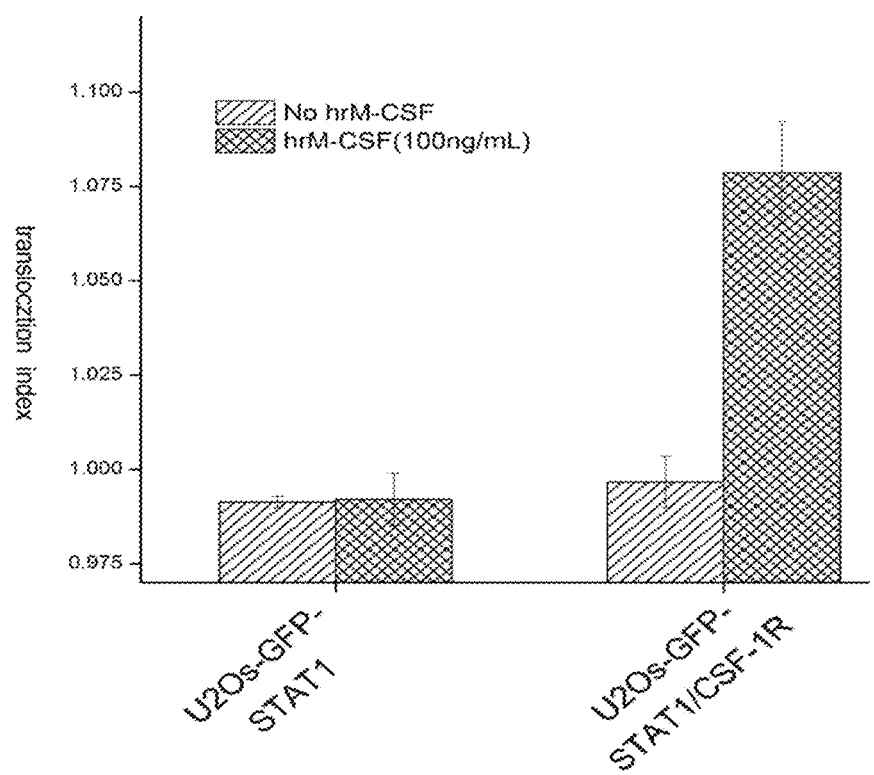

In the presence of hrM-CSF at a concentration of 100 ng/mL, significant GFP-STAT1 nuclear translocation occurred in the U2OS-GFP-STAT1/CSF-1R cells expressing human c-Fms, as compared to the U2OS-GFP-STAT1 cells expressing no human c-Fms (FIG. 1A-B).

Example 3: Determination of the Median Effective Concentration of hrM-CSF for Inducing GFP-STAT1 Nuclear Translocation The steps were as follows:
1) using the cells prepared in the Example 1 to prepare a cell suspension of $1\times10^5$ cells/mL, seeding the cells to a 96-well culture plate (which was black and transparent at the bottom) at 100 μL/well;
2) culturing the cells in an incubator at 37° C., 5% $CO_2$, 80% humidity for 24 hours;
3) washing the cells twice with the cell analytic liquid at 100 μL/well for each time, discarding the solution, and adding the cell analytic liquid at 50 μL/well;
4) adding hrM-CSF diluted with the cell analytic liquid, to obtain a final concentration of 1, 3, 10, 30, 100, 300, 600, 1000 ng/mL respectively;
5) after incubating the cells in an incubator at 37° C., 5% $CO_2$, 80% humidity for 30 minutes, adding the cell fixation solution preheated at 37° C. at 100 μL/well, slightly shaking the culture plate to mix the mixture uniformly, and placing the plate in dark at room temperature for 20 minutes;
6) discarding the solution, adding 1×PBS solution that contains hoechst33342 at 200 μL/well, and placing the plate in dark at room temperature for 30 minutes; and
7) obtaining the cell image by using In Cell Analyzer 2000, and analyzing the extent of nuclear translocation of GFP-STAT1 by using Nuclear Trafficking Analysis Module.

Figure 2A:
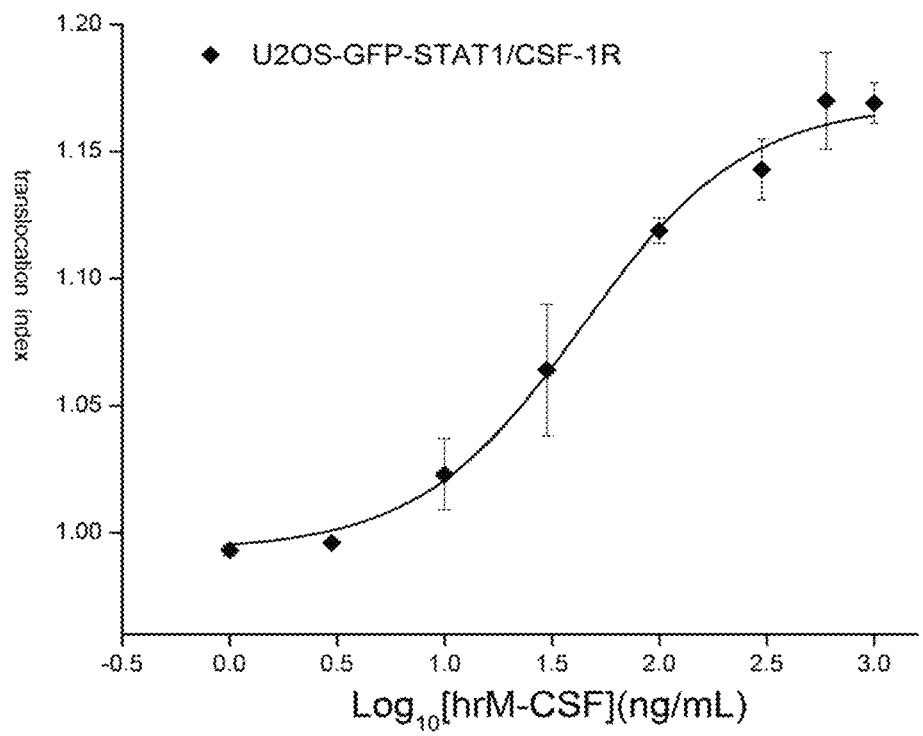
FIG. 2: The dose-effect relationship of GFP-STAT1 nuclear translocation induced by hrM-CSF. n=6, $EC_{50}$ is 43.50±3.68 ng/mL (FIG. 2A-B).
Figure 2B:
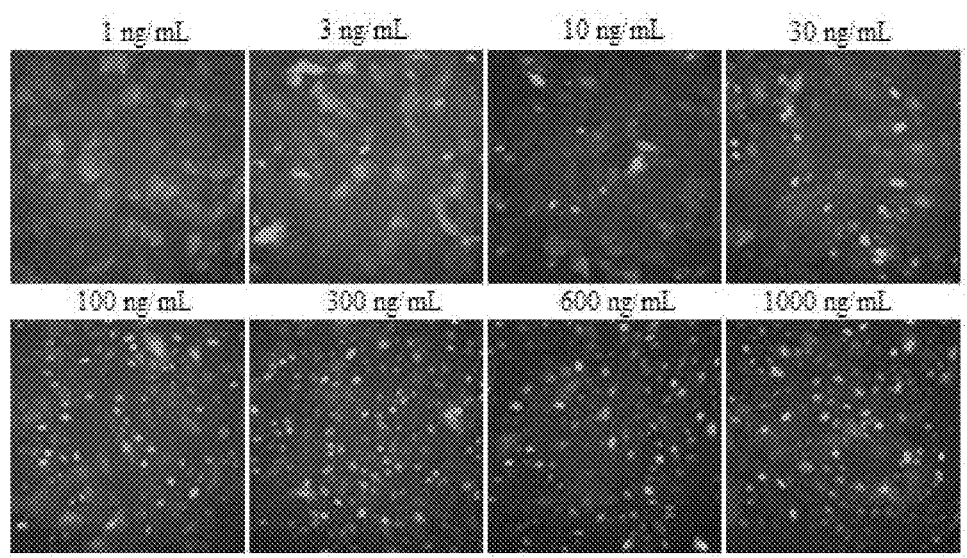

As shown in FIG. 2A-B, when the concentration of hrM-CSF was 10 ng/mL, nuclear translocation of GFP-STAT1 fusion protein began; when the concentration of hrM-CSF was 600 ng/mL, the extent of nuclear translocation of GFP-STAT1 reach the maximum. The "S"-type curve was fitted by Origin 7.5 software sigmoidal Fit to obtain the median effective concentration ($EC_{50}$) of hrM-CSF, at which the c-Fms kinase in the U2OS-GFP-STAT1/CSF-1R cells was activated to induce GFP-STAT1 nuclear translocation, and which was 43.50±3.68 ng/mL.

Example 4: Evaluation of the Reliability of the U2OS-GFP-STAT1/CSF-1R Cell Model In this example, the reliability of the new cell model established in the example 1 was evaluated by Z' factor. Z' factor, as an important parameter for evaluating reliability of an experimental system, is widely applicable when evaluating the stability and reliability of high-throughput screening, high content analysis experimental systems. Z' factor is calculated according to the following formula:

$$Z' = 1 - \frac{(3\sigma_{C+} + 3\sigma_{C-})}{|\mu_{C+} - \mu_{C-}|}$$

wherein σ represents standard deviation, μ represents mean signal, C+ represents positive control, C− represents negative control.

Z' factor is within 0~1. When Z' is 0, it indicates that the experimental system is not tenable. When 0.5>Z'>0, it indicates that the experimental system has poor stability and is not reliable. When 1>Z'≥0.5, it indicates that the experimental system has good stability and reliability. If Z' factor is 1, then the standard deviation between positive control and negative control is 0, which indicates an ideal experimental system (Ji-Hu Zhang, Thomas D. Y. Chung and Kevin R. Oldenburg. A Simple Statistical Parameter for Use in Evaluation and Validation of High Throughput Screening Assays [J]. *J Biomol. Screen.* 1999.4: 67).

The steps for evaluating the reliability of the experimental system established in the present invention were as follows:
1) preparing a cell suspension of $1\times10^5$ cells/mL, seeding the cells to a 96-well culture plate (which was black and transparent at the bottom) at 100 μL/well, and culturing the cells in an incubator at 37° C., 5% $CO_2$, 80% humidity for 24 hours;
2) washing the cells twice with the cell analytic liquid at 100 μL/well for each time, discarding the solution, and adding the cell analytic liquid at 50 μL/well;
3) adding hrM-CSF diluted with the cell analytic liquid, to obtain a final concentration of 200 ng/mL, setting the cell analytic liquid containing no hrM-CSF as the control, and incubating the cells in an incubator at 37° C., 5% $CO_2$, 80% humidity for 30 minutes;
4) adding the cell fixation solution preheated at 37° C. at 100 μL/well, slightly shaking the culture plate to mix the mixture uniformly, and placing the plate in dark at room temperature for 20 minutes;
5) discarding the solution, adding 1×PBS solution that contains hoechst33342 at 200 μL/well, placing the plate in dark at room temperature for 30 minutes;
6) obtaining the cell image by using In Cell Analyzer 2000, analyzing the extent of nuclear translocation of GFP-STAT1 by using Nuclear Trafficking Analysis Module, and calculating the Z' factor.

Figure 3:
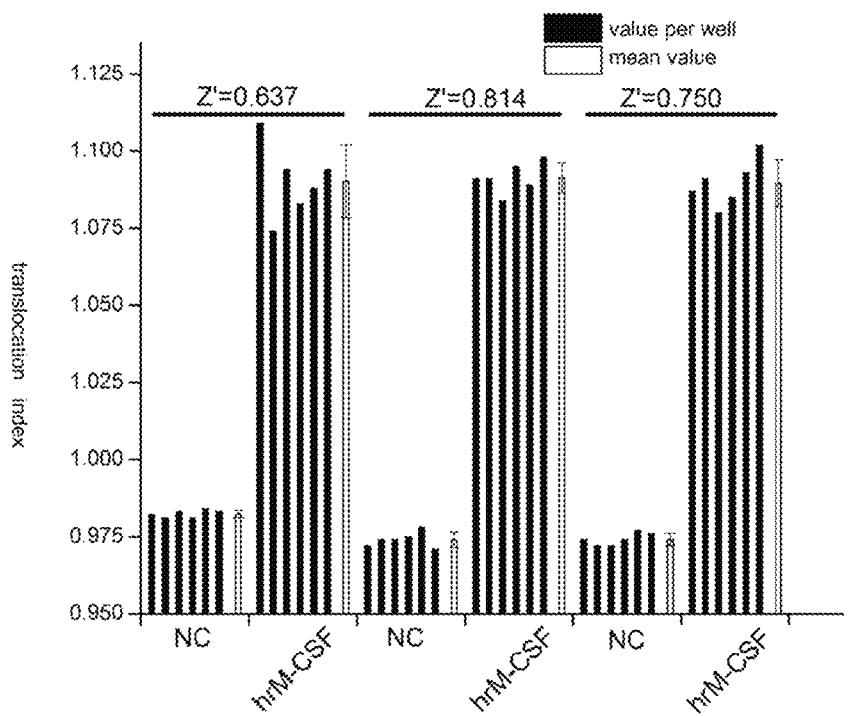
FIG. 3: Reliability analysis of the drug screening system based on GFP-STAT1 nuclear translocation induced by hrM-CSF. n=6, the mean Z' value is 0.734.

In the presence of 200 ng/mL hrM-CSF, the screening system established in the present invention had a mean Z' factor of 0.734 (FIG. 3).

The result shows that the cell of the present invention is very reliable and feasible as a cell model for screening tyrosine kinase inhibitors or evaluating the inhibiting activity of a compound against tyrosine kinase.

Example 5: The Effect of the Time for Treating Cells with hrM-CSF on GFP-STAT1 Nuclear Translocation The steps were as follows:
1) using the cells prepared in the example 1 to prepare a cell suspension of $1\times10^5$ cells/mL, seeding the cells to a 96-well culture plate (which was black and transparent at the bottom) at 100 μL/well; and culturing the cells in an incubator at 37° C., 5% $CO_2$, 80% humidity for 24 hours;
2) washing the cells twice with the cell analytic liquid at 100 μL/well for each time, discarding the solution, and adding the cell analytic liquid at 50 μL/well;
3) adding hrM-CSF diluted with the cell analytic liquid every 5 minutes, to obtain a final concentration of 200 ng/mL, setting the cell analytic liquid containing no hrM-CSF as the control, incubating the cells in an incubator at 37° C., and treating the cells with the cytokine for 0, 5, 10, 15, 20, 25, 30, 35, 40, 45, 50, 55, 60 minutes, respectively;
4) adding the cell fixation solution preheated at 37° C. at 100 μL/well, slightly shaking the culture plate to mix the mixture uniformly, and placing the plate in dark at room temperature for 20 minutes;
5) discarding the solution, adding 1×PBS solution that contains hoechst33342 at 200 μL/well, and placing the plate in dark at room temperature for 30 minutes; and 6) obtaining the cell image by using In Cell Analyzer 2000, and analyzing the extent of nuclear translocation of GFP-STAT1 by using Nuclear Trafficking Analysis Module.

Figure 4:
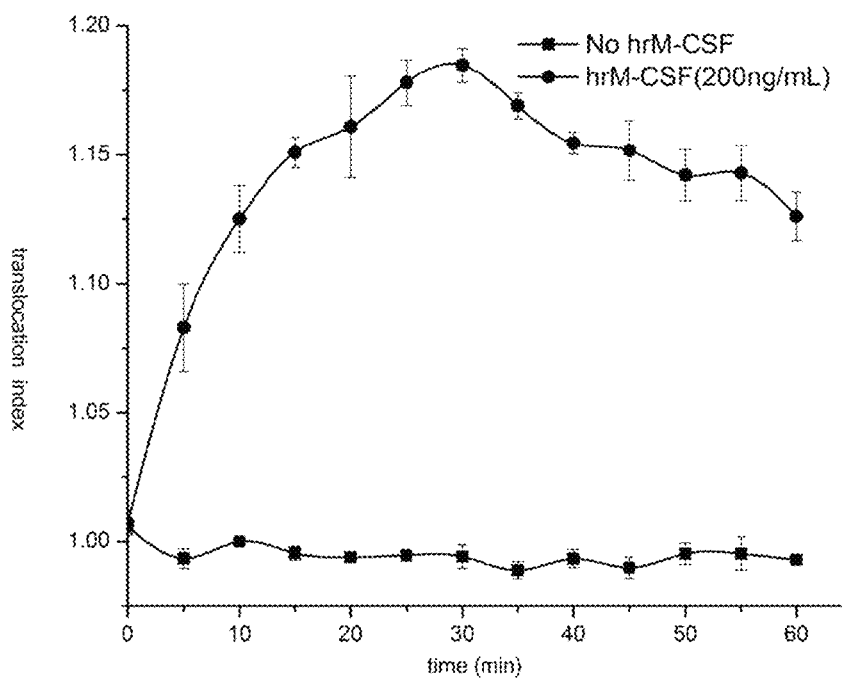
FIG. 4: The effect of the time for treating cells with hrM-CSF on GFP-STAT1 nuclear translocation.

Once hrM-CSF factor was added, the GFP-STAT1 nuclear translocation quickly occurred. During the period while the cells were treated with the factor from 5 to 30 minutes, the extent of GFP-STAT1 nuclear translocation increased continuously. At the point of 30 minutes, the extent of GFP-STAT1 nuclear translocation reached the maximum. After 30 minutes, as the time for treating the cells with the factor increased, the extent of GFP-STAT1 nuclear translocation reduced gradually instead (FIG. 4).

Example 6: The Effect of the Cell Seeding Density on GFP-STAT1 Nuclear Translocation The steps were as follows:
1) seeding the cells prepared in the example 1 to a 96-well culture plate (which was black and transparent at the bottom), at 1000, 2000, 4000, 6000, 8000, 10000, 12000, 14000 cells/mL respectively, and culturing the cells in an incubator at 37° C., 5% $CO_2$, 80% humidity for 24 hours;
2) washing the cells twice with the cell analytic liquid at 100 μL/well for each time, discarding the solution, and adding the cell analytic liquid at 50 μL/well;
3) adding hrM-CSF diluted with the cell analytic liquid at 50 μL/well, to obtain a final concentration of 200 ng/mL, setting the cell analytic liquid containing no hrM-CSF as the control, and incubating the cells in an incubator at 37° C. for 30 minutes;
4) adding the cell fixation solution preheated at 37° C. at 100 μL/well, slightly shaking the culture plate to mix the mixture uniformly, and placing the plate in dark at room temperature for 20 minutes;
5) discarding the solution, adding 1×PBS solution that contains hoechst33342 at 200 μL/well, and placing the plate in dark at room temperature for 30 minutes; and
6) obtaining the cell image by using In Cell Analyzer 2000, and analyzing the extent of nuclear translocation of GFP-STAT1 by using Nuclear Trafficking Analysis Module.

Figure 5:
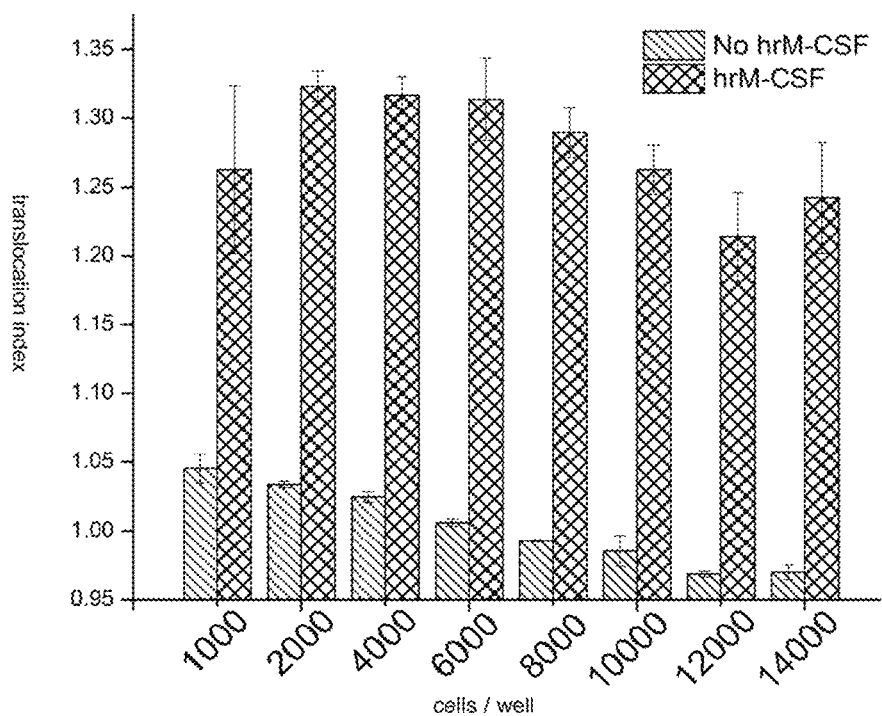
FIG. 5: The effect of the seeding density of U2OS-GFP-STAT1/CSF-1R cells on GFP-STAT1 nuclear translocation.

As shown in FIG. 5, when the cell seeding density increased from 2000 cells/well to 12000 cells/well and the cells were treated with 200 ng/mL hrM-CSF for 30 minutes, the induced extent of the GFP-STAT1 nuclear translocation reduced gradually. However, the reduction was not significant. The ratio of the mean fluorescence intensity of nucleus to the mean fluorescence intensity of cytoplasm in the blank control cells reduced as the cell seeding density increased.

Example 7: The Inhibitory Effect of GW2580 on GFP-STAT1 Nuclear Translocation in the Cell Model GW2580 is a selective macrophage colony stimulating factor receptor kinase inhibitor, which can effectively inhibit the phosphorylation of the receptor kinase. The c-Fms inhibitor screening model established in the Example 1 was used to evaluate the inhibitory activity of GW2580. The steps were as follows:
1) seeding the U2OS-GFP-STAT1/CSF-1R cells to a 96-well culture plate (which was black and transparent at the bottom), at $1.0 \times 10^4$ cells/mL, and culturing the cells in an incubator at 37° C., 5% $CO_2$, 80% humidity for 24 hours;
2) discarding the medium, and washing the cells twice with the cell analytic liquid at 100 μL/well for each time,
3) adding the cell analytic liquid at 50 μL/well; adding GW2580 dissolved in DMSO which was diluted with the cell analytic liquid at 50 μL/well, and incubating the cells in an incubator at 37° C., 5% $CO_2$, 80% humidity for 1 hour;
4) adding the cell analytic liquid that contains hrM-CSF at 25 μL/well, to obtain a final hrM-CSF concentration of 200 ng/mL, and incubating the cells in an incubator at 37° C., 5% $CO_2$, 80% humidity for 30 minutes;
5) adding the preheated formaldehyde (8%) diluted with 1×PBS solution at 125 μL/well, and placing the plate in dark at room temperature for 20 minutes;
6) discarding the solution, adding 1×PBS solution that contains hoechst33342 at 200 μL/well, and placing the plate in dark at room temperature for 30 minutes; obtaining the cell image by using In Cell Analyzer 2000, analyzing the extent of nuclear translocation of GFP-STAT1 by using Nuclear Trafficking Analysis Module; and fitting the "S"-type curve by Origin7.5 software sigmoidal Fit and calculating the $IC_{50}$ value.

Figure 6:
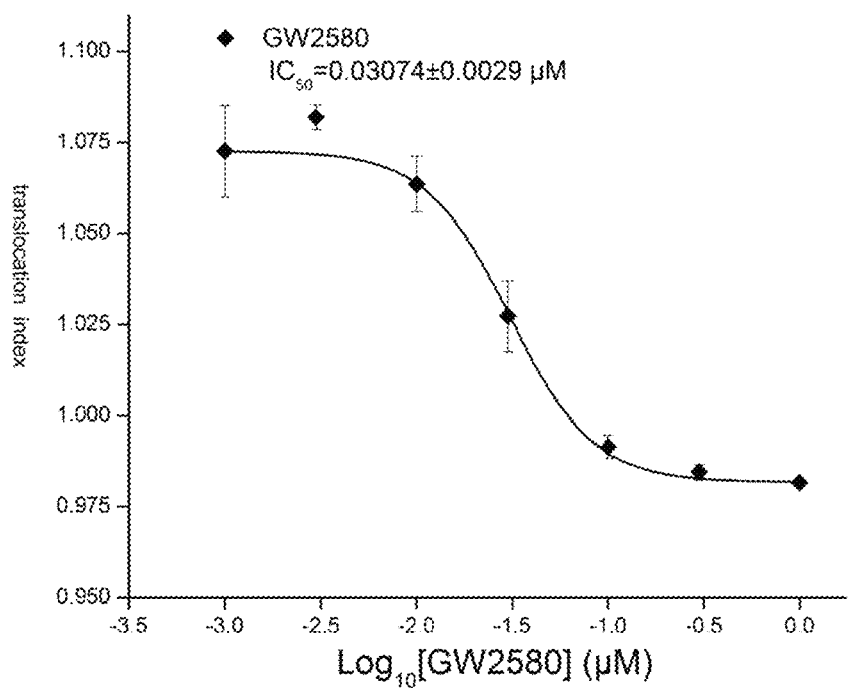
FIG. 6: A drawing shows the inhibitory effect of c-Fms inhibitor GW2580 on nuclear translocation in the cell model wherein GFP-STAT1 nuclear translocation is induced by hrM-CSF. (n=3; $IC_{50}$ of GW2580 is 30.74±2.9 nM).

The result was shown in FIG. 6. In the cell model for screening c-Fms inhibitors wherein hrM-CSF activated human c-Fms and induced GFP-STAT1 nuclear translocation, GW2580 could significantly inhibit GFP-STAT1 nuclear translocation (n=3; $IC_{50}$=30.74±2.9 nM).

Figure 7:
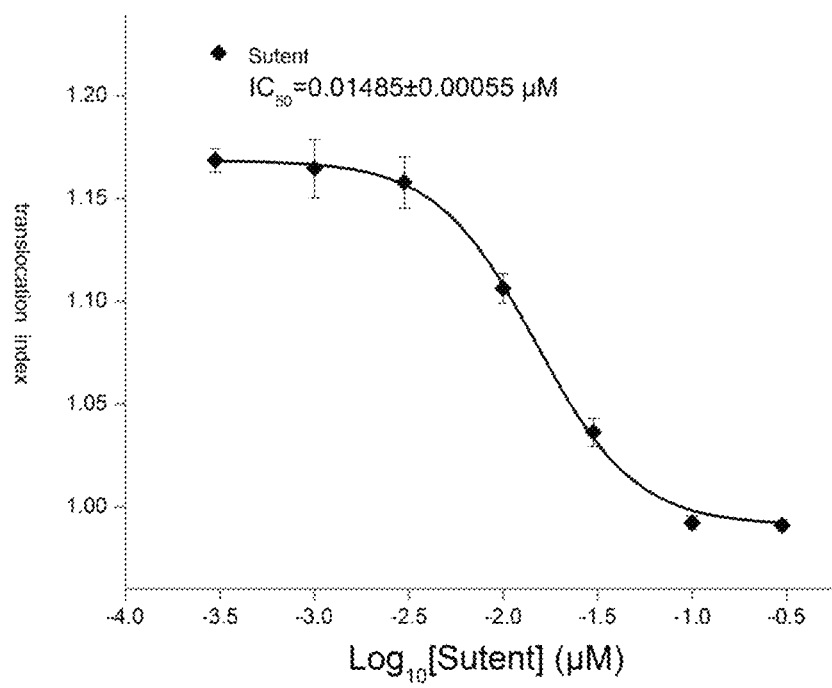
FIG. 7: A drawing shows the inhibitory effect of tyrosine kinase inhibitor Sutent on nuclear translocation in the cell model wherein GFP-STAT1 nuclear translocation is induced by hrM-CSF. (n=3; $IC_{50}$ of Sutent is 14.85±0.55 nM).

Example 8: The Inhibitory Effect of Sutent on GFP-STAT1 Nuclear Translocation in the Cell Model Sunitinib (SU11248, Sutent) is a multiple-targeted tyrosine receptor kinase inhibitor, and its main targets are vascular endothelial growth factor receptor (VEGFR), PDGFR, c-Kit. In clinical practice, sunitinib is mainly used to treat cancers such as malignant renal cell carcinoma, and gastrointestinal stromal tumor resistant to Imatinib. It is reported in literature that sunitinib can also effectively inhibit phosphorylation of c-Fms (Guo J, Marcotte Pa., McCall J O, et al. Inhibition of phosphorylation of the colony-stimulating factor-1 receptor (c-Fms) tyrosine kinase in transfected cells by ABT-869 and other tyrosine kinase inhibitors[J]. Mol. Cancer Ther. 2006, 5(4):1007-1013). Therefore, the inhibitory activity of sutent was evaluated by using the cell model for screening c-Fms inhibitors as established in the example 1. The activity of sutent was evaluated by using a method similar to that in example 7. The result showed that sutent could also effectively inhibit GFP-STAT1 nuclear translocation (n=3; $IC_{50}$=14.85±0.55 nM, as shown in FIG. 7).

Figure 8:
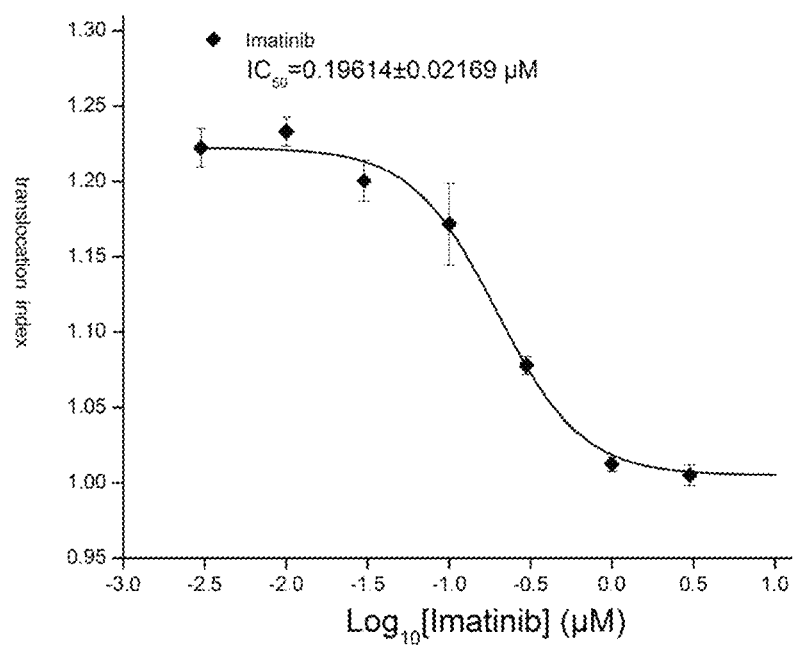
FIG. 8: A drawing shows the inhibitory effect of tyrosine kinase inhibitor Imatinib on nuclear translocation in the cell model wherein GFP-STAT1 nuclear translocation is induced by hrM-CSF. (n=3; $IC_{50}$ of Imatinib is 196.1±21.7 nM).

Example 9: the Inhibitory Effect of Imatinib on GFP-STAT1 Nuclear Translocation in the Cell Model Imatinib is a tyrosine kinase inhibitor developed by Novartis International AG, and is mainly used to treat myelogenous leukemia abnormally expressing Bcr-ab1 and gastrointestinal stromal tumor with abnormal c-Kit activity in clinical practice. The activity of imatinib was evaluated by using a method similar to that in example 7. The result showed that imatinib could also effectively inhibit GFP-STAT1 nuclear translocation (n=3; $IC_{50}$=196.1±21.7 nM, as shown in FIG. 8).

Although the specific modes for carrying out the Invention are described in detail, the skilled in the art would understand that various amendments and replacements may be made to the details on the basis of all the disclosed teachings, and the changes are within the scope of the present invention. The scope of the invention is defined by the attached claims and any equivalent thereof.

The invention claimed is:
1. A cell strain, which was deposited in China General Microbiological Culture Collection Center, with an accession number of CGMCC No. 4688, and a deposit date of Mar. 22, 2011.

* * * * *